United States Patent [19]

Richou et al.

[11] Patent Number: 5,479,816
[45] Date of Patent: Jan. 2, 1996

[54] METHOD OF PHYSICAL-CHEMICAL ANALYSIS BASED ON THE CONTROL OF INTERFACE TENSIONS, AND CORRESPONDING APPARATUS

[75] Inventors: Jacques Richou; Michel Grimaldi, both of Toulon; Robert Verger, Marseille; Claude Riviere, Marseille; André Bois, Marseille; Sylvie Nury, Fourqueux, all of France

[73] Assignee: Universite de Toulon et du Var, Laboratoire d'Optoelectronique, Lar Garde, France

[21] Appl. No.: 117,177

[22] PCT Filed: Mar. 12, 1992

[86] PCT No.: PCT/FR92/00227

§ 371 Date: Apr. 22, 1994

§ 102(e) Date: Apr. 22, 1994

[87] PCT Pub. No.: WO92/16824

PCT Pub. Date: Oct. 1, 1992

[30] Foreign Application Priority Data

Mar. 14, 1991 [FR] France ................................ 91 03105

[51] Int. Cl.[6] ............................................ G01N 13/02
[52] U.S. Cl. ............................................ 73/64.48; 73/64.52
[58] Field of Search ............................ 73/64.48, 64.52, 73/64.55

[56] References Cited

U.S. PATENT DOCUMENTS

| | | | |
|---|---|---|---|
| 2,819,611 | 1/1958 | Shellard et al. | 73/64.52 |
| 3,483,737 | 12/1969 | Jennings, Jr. et al. | 73/64.52 |
| 4,196,615 | 4/1980 | Davis | 73/64.4 |
| 4,646,562 | 3/1987 | Cronan | 73/64.4 |
| 4,874,426 | 10/1989 | Honda | 73/64.4 |
| 4,953,389 | 9/1990 | Schurch | 73/64.4 |
| 5,218,841 | 6/1993 | Hool | 73/64.52 |

FOREIGN PATENT DOCUMENTS

| | | | |
|---|---|---|---|
| 0153229 | 12/1981 | Germany | 73/64.48 |
| 1774229 | 11/1992 | U.S.S.R. | 73/64.48 |
| 2092758 | 8/1982 | United Kingdom | 73/64.52 |

Primary Examiner—Thomas P. Noland
Assistant Examiner—J. David Wiggins
Attorney, Agent, or Firm—Nilles & Nilles

[57] ABSTRACT

Process and apparatus for analyzing the characteristics of a liquid/fluid interface, especially in the presence of surface-active agents. A tensiometer operates according to the principle of the suspended drop and the amount of liquid injected in the drop is adjusted according to the value of the calculated interface tension; the volume of the formed drop is progressively increased as the interface tension tends to diminish. A drop-forming device (30) can acquire an image of the drop and read the drop contour (40), can calculate the interface tension based on the shape and the size of the contour, and can adjust the same. A method of high speed measurement of interface tension uses all the points in the drop contour and provides a value in less than a second with the aid of a microcomputer.

15 Claims, 4 Drawing Sheets

FIG_1

FIG_2

FIG_3

FIG_4

FIG_5

FIG_6

METHOD OF PHYSICAL-CHEMICAL ANALYSIS BASED ON THE CONTROL OF INTERFACE TENSIONS, AND CORRESPONDING APPARATUS

The interface tension between two non-miscible liquids, or between a liquid and an ambient fluid, is a physical magnitude that is much used in various scientific and technical fields. It represents the energy brought into play by the forces of intermolecular cohesion on an interface between a liquid and an ambient medium. An ambient medium is a medium, which is also fluid, into which the liquid considered is plunged. The liquid and the ambient medium are non-miscible. In very concrete terms, it is the force that tends to collect the liquids together into drops whose shape would be spherical if they were not deformed by gravity.

Interface tension is expressed in terms of force per unit of length, for example in Newton/m or millinewton/m.

For a given pair constituted by a pure liquid and a pure ambient medium, under fixed conditions of temperature and pressure, the interface tension is a constant magnitude.

However, the presence of certain chemical agents on the interface may modify the structure of the interface and, consequently, the value of the interface tension. These agents are then known as surface-active agents.

The measurement of the interface tensions may then serve to assess the surfactant activity of certain chemical agents or, indirectly, to measure the concentration of these agents in a liquid.

These measurements find numerous applications, notably in the petroleum, chemical, food, cosmetic and other industries.

For example, these measurements are useful for the developing of efficient detergents or emulsifiers; they are useful for the development of products to disperse crude petroleum in the event of oil slicks; and again they are useful for the study of enzymatic physiological reactions.

There is a known way of calculating the value of the interface tension between a liquid and an ambient medium on the basis of the measurements (optical measurements) of the shape and dimensions of a drop of liquid with vertical axial symmetry, plunged into the ambient medium and clinging to the end of a hollow needle used to form the drop.

The drop takes a shape that results from the equilibrium among the forces of gravity, buoyancy, the forces of interface tension and the pressure due to the curvature of the interface.

It can thus be seen that, for two given liquids, the separation of the drop from its own medium depends on the interface tension of the radius of the hollow needle and on the angle of contact. This angle is directly related to the material constituting the needle.

By analyzing the shape and dimensions of the drop, it is possible to determine the value of the interface tension in an absolute way. There is indeed a relationship between the value of the interface tension and the geometrical parameters characterizing the shape of the drop. This relationship is defined by an equation known as the Laplace equation.

This is what is called the calculation of the interface tension by the "pendant drop" method. There is also a known way of carrying out this calculation using the shape of a drop laid on a horizontal solid surface.

However, the Laplace equation does not allow for an analytical approach to the obtaining of the value of the interface tension. It can therefore be resolved only in an indirect way.

Two major types of approaches have been used in the past to obtain a value of the interface tension on the basis of the knowledge of the shape of the drop. The first method, which is speedy but has little precision, consists in determining the position of two characteristic points of contour in order to deduce an approximate value of the interface tension therefrom. The second method, which is more precise but slower, consists in using all the points of the contour of the drop and in carrying out successive approximations until a value of tension is found for which the theoretical shape of the drop is as close as possible to the real shape.

The standard approaches used to determine the interface tension by the method of the pendant drop or the standing drop are described in the various documents. For example, the article by H. H. GIRAULT, D. J. SCHIFFRIN and B. D. SMITH, "The Measurement of Interfacial Tension of Pendant Drops Using a Video Image Profile Digitizer", in *Journal of Colloid and Interface Science*, vol. 101, No. 1, September 1984 gives a detailed description of the formulae on which these calculations are based.

The article by the same authors, "Drop Image Processing for Surface and Interfacial Tension Measurements", in *Journal of Electroanalysis Chemistry*, 137, pp. 207, 217, 1982, also gives all the details on the calculations of interface tension by the method of the pendant drop.

In the prior art, what has been observed is that it is not only the absolute value of the interface tension that could be useful but also the variation of this tension under the effect of surface-active agents. Studies have shown, in particular, that there is a very narrow correlation between the concentration of surface-active agent in the ambient medium and the initial speed of variation of the interface tension at the time of the formation of the drop. It is therefore possible to measure a very important parameter, namely the surfactant capacity of an agent or the concentration of this agent in the medium (or the drop) if it is possible to measure the initial speed of variation of the interface tension.

One of the problems encountered is that it is not possible to measure this initial speed directly. To obtain it, it is necessary first of all to make calculations, at regular time intervals, of the value of the interface tension, on the basis of the shape of the drops at these instants (as and when this shape varies owing to the action of the surface-active agents); then it is necessary to carry out a point-by-point plotting of a curve of variation of the calculated tension; and finally, this curve has to be extrapolated towards the starting point in order to deduce the initial speed therefrom.

This is a very slow method, especially if the interface tension is measured by the precise method of comparison of the theoretical profile and the real profile of the drop.

This is why a new method is proposed herein for the analysis of the behavior of an interface between a liquid and a fluid in which this liquid is not miscible. The method according to the invention is a dynamic method, i.e. it is concerned not chiefly with temporally stable characteristics but above all with the progress of these characteristics in tandem with a process that it is sought to study.

According to the invention, there is proposed a method that consists in introducing a liquid in a controlled way into an ambient medium, in calculating the interface tension and in acting on a unit for the introduction of the liquid in a direction that tends to bring the interface tension to a desired value.

In practice, a drop of liquid will be formed in an ambient medium from a needle that penetrates the ambient medium, the interface tension between the liquid and the ambient medium will be calculated from the measurements made on the drop, and the introduction of liquid by the needle will be servocontrolled as a function of the calculated interface tension.

The invention therefore is essentially based on the idea of controlling the quantity of liquid injected to form the drop, as a function of the calculated interface tension whereas, until now, analyses were made from a drop with a constant volume.

The measurement is then dynamic: if the calculated interface tension tends to get modified, action will be taken on the injection needle for the modification, as needed, of the quantity of liquid injected, the aim being to keep the interface tension at a desired value.

In practice, it will be sought to keep the interface tension at a constant value, at least during a part of the experiment, but it is also possible to conceive of cases where the injection of liquid is servocontrolled to make the interface tension follow a desired relationship.

This method according to the invention is therefore quite particularly suited to the real-time analysis of the behavior of surface-active agents: the surface-active agent tends to modify the interface tension owing to the adsorption of the agent on the surface of the drop. With the regulation system according to the invention, it is possible swiftly to increase the external surface area and the volume of the drop of liquid so as to tend to keep the interface tension constant despite the adsorption of product on the surface. This increase of surface area indeed gives rise to an effect of new free surfaces to which the surface-active agents may get fixed. The real behavior of the surface-active agent can therefore be evaluated far more efficiently than when a single drop is gradually covered with the surface-active agent. In particular, it is possible to assess the quantity of agent adsorbed per time unit on a free interface.

In a concrete example of use, the following procedure is used: a drop is formed, the value of the interface tension of the drop is calculated at determined successive instants, without action on the injection of liquid and then, at a given instant, the interface tension calculated at this time is established and stored as a set-point value of interface tension; finally, from this point onwards, the action of the injection unit is permitted in a direction tending to keep the interface tension calculated at each instant at this set-point value.

The invention also proposes an analyzing apparatus for the implementation of the invention. The apparatus has a means to form a drop of liquid in an ambient medium, a means to analyze the shape and dimensions of the drop, a means to calculate the interface tension from these measurements and a means to servocontrol the quantity of liquid introduced according to the interface tension calculated. The means to modify the quantity of liquid comprises for example a syringe connected to a needle penetrating the ambient medium, and a stepping motor to activate the syringe.

The means to analyze the shape and the dimensions of the drop are optical and electronic means.

This idea of servolinking the quantity of liquid to the interface tension can be implemented on condition that the interface tension is calculated in real time: it must be possible to modify the quantity of liquid injected as soon as it is perceived that the interface tension is diverging from the set-point value.

This is why it is very important to have a swift method of measurement. Calculation based on two points of the contour of the drop is possible (see the above-mentioned articles). However, it is insufficiently precise and sometimes it can be applied solely to particular shapes of drops (drops with inflexion points that are about to separate from the needle).

Conversely, the methods of measurement based on the use of the coordinates of all the points of the contour are more precise but far slower. They make use of a iterative comparison of calculated contours and of the real contour of the drop. In short, it can be said that the interface tension is obtained as follows: the exact shape of the drop is measured with a video camera and a digital processing operation carried out on the signal coming from the camera; a theoretical drop shape is calculated as a function of a variable unknown parameter which is the interface tension, a parameter to which there is given an initial value which, if possible, approaches the expected value of interface tension. The theoretical shape and the real shape are compared, preferably by using the least error squares method. The unknown parameter is modified and the calculatation is reiterated until the theoretical shape corresponds as closely as possible to the real shape of the drop. The value of interface tension is then the one that makes theory correspond best to reality.

It will be seen that this method is very slow: a computer with a slow processor will take several seconds before finding a fairly precise value. However, the result is more precise than with a method that uses only two points.

It would be desirable, in many cases, to have high precision while at the same time greatly reducing the period of time taken to obtain the measurement.

This is why there is proposed, according to a second aspect of the invention, a new method for the calculation of interface tension that can be used notably in the regulation method indicated here above.

Herein, there is proposed a method for the measurement of interface tension in which there is used a method of calculation that does not draw upon iterative comparisons of calculated and real shapes of drops and that, nevertheless, uses all the points of the contour and not only two points or some points like the fast methods known to date.

The method comprises the following operations:

the optical determination of the shape of a drop of a liquid in an ambient medium and, notably, the extraction of the coordinates of the points of the digitized contour of the drop;

for each point with an index i of the digitized contour, having horizontal and vertical coordinates $x_i$ and $z_i$ from the tip of the drop: calculation of three values $u_i$, $v_i$, $w_i$ bringing into play only the coordinates of the point i, the volume of the drop between the tip and the ordinate plane $z_i$, and the angle with respect to the horizontal of a tangent to the drop at the point i;

summation for all the points i of at least five of the following squares and products: $u_i^2$, $v_i^2$, $w_i^2$, $u_i v_i$, $v_i w_i$, $w_i u_i$, the summations giving respectively sums S1, S2, S3, S5, S6.;

resolution of a system of two linear equations with two unknown quantities A and B taken from among the following three values:

$$A.S1+B.S3=S5$$

$$A.S3+B.S2=S4$$

$$A.S5+B.S4=S6$$

calculation of the interface tension from A and from known constants which are the constant of gravity g and the difference in density between the drop and the ambient medium.

This method according to the invention thus does not make use of an iterative comparison of calculated shapes and the real shape of the drop, and yet it uses all the points of the contour.

A detailed example of the implementation of this method, applied to a pendant drop, shall be given here below, it being understood that this method can also be applied to a standing drop. It will be seen in particular that the values $u_i$, $v_i$, $w_i$ may respectively be:

$u_i$: the difference between, firstly, the partial volume of the drop divided by the number Pi and, secondly, the product $x_i^2 \cdot z_i$ $v_i$: the square $x_i^2$ $w_i$: the product of $x_i$ by the sine of the angle E formed with the horizontal by the tangent to the contour at the index i point.

The interface tension is then equal to g(D1-D2)/2A where D1-D2 represents the difference between the densities of the drop and of the ambient medium.

The method according to the invention is very swift and can be used to obtain a value of tension in less than one second with a personal microcomputer, with a precision that is practically equal to that obtained in the method of iterative approximation of a calculated contour and a real contour. A personal microcomputer is, for example, a microcomputer of the so-called IBM compatible type, provided with a 286 type microprocessor from the American firm INTEL CORPORATION, assisted by a 287 type arithmetical coprocessor by the same firm, and a working memory of 640 kbytes. This method may be used to make not only precise measurements of interface tensions or curves of variation of interface tensions but also very advantageously in the regulation method described here above.

Other features and advantages of the invention shall appear from the following detailed description, made with reference to the appended figures, wherein:

FIG. 1 shows a pendant drop at the end of an injection needle;

FIG. 2 shows the development of the shape of a drop in a surface-active medium;

FIG. 3 shows typical curves of variation of interface tension in the presence of surface-active agents;

FIG. 4 shows the principle of the invention;

FIG. 6 shows the variables used to calculate the tension.

FIG. 1 shows an exemplary view of a drop of liquid 10, hanging at the end of a needle 12 that has been used to convey the liquid to form the drop. The drop is immersed in a fluid 11 (generally another liquid in which the first one is non-miscible). The shape of the drop is the resultant of the equilibrium between the forces of gravity (which tends to stretch the drop) and the forces of cohesion due to the interface tension, which tend to reduce the drop to a spherical shape.

The invention can work with drops that hang downwards (predominance of gravity with respect to buoyancy) or upwards (predominance of buoyancy).

FIG. 2 shows the gradual deformation of the drop in time under the effect of surface-active agents. The drop gets elongated: at the end of a certain period of time, it may even get detached from the needle. The period of stay of the drop on the needle has, besides, been used to assess the concentration of the ambient medium in surface-active agents.

It will be noted that the invention can be applied when the surface-active agent is contained in the ambient medium, or when it is contained in the drop itself.

FIG. 3 shows typical curves of variation of the interface tension as a function of time, in the presence of surface-active agents. It can be seen that the interface tension diminishes gradually under the action of the surface-active agent. This is typically the case, for example, in an enzymatic reaction of lipases on a drop of vegetable oil. The three curves shown correspond to different dosages of surface-active agent in the ambient medium.

The original method of analysis according to the invention is recalled with reference to FIG. 4. It consists in modifying the quantity of liquid present in the drop as a function of a calculation of interface tension done in real time on the basis of the dimensions of the drop.

The measurement of the variations of the quantity of liquid is a very valuable indication of the kinetics of the reaction. In particular, it gives a good evaluation of the speed of migration of the surface-active agent towards the interface between the drop and the ambient medium: as and when liquid is injected, new contact surfaces become available between the liquid and the ambient medium; the surface-active agent migrates on these surfaces while the rest of the interface is relatively encumbered by the products of the reaction. The measurement of the flow rate of the liquid is therefore highly representative of the activity of the agent (or of its concentration). This measurement of flow rate can easily be obtained from the shape and dimensions of the drop which, in any case, are necessary for the real-time calculation of the interface tension.

The method that will be used in practice will consist essentially in servo-controlling the flow rate in such a way that the interface tension remains constant and equal to a set-point value. The set-point value could be a value calculated from the shape of the drop at the start of the experiment.

Figure 5:
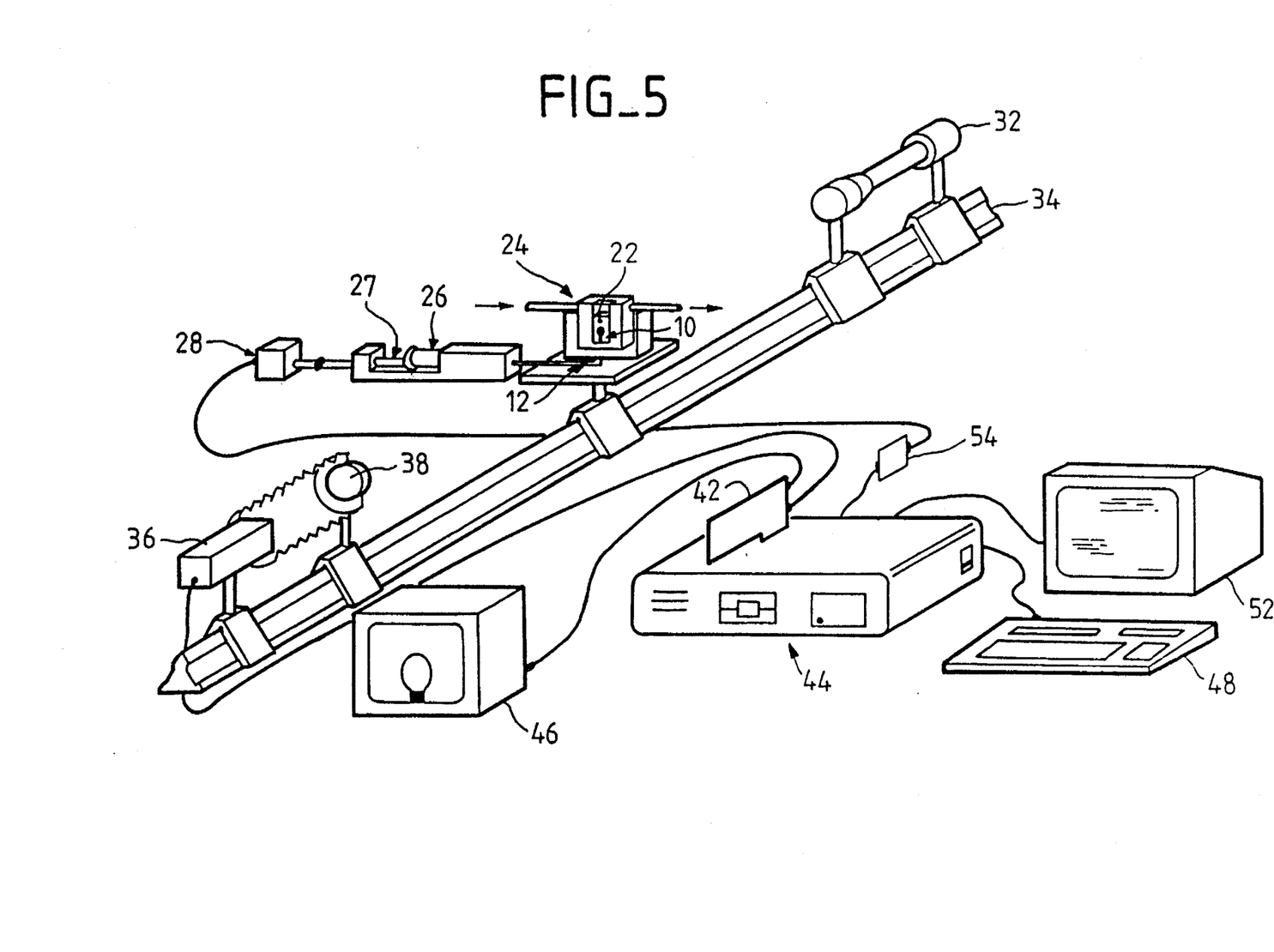
FIG. 5 shows a practical implementation of the invention.

FIG. 4 gives a simple and symbolic reminder of what has to be provided for in principle: a drop forming mechanism 20 capable of being activated to inject a variable quantity of liquid during the experiment, a device 30 for the acquisition of the image of the drop, a means 40 to extract the shape and dimensions of the drop from the acquired image, a means 50 to calculate the interface tension from the shape and dimensions of the drop and a control mechanism 60 receiving the calculated value of tension and a set-point value (in principle constant) and acting on the drop-forming mechanism. In FIG. 4, the set-point value is shown as being given independently of the tension calculation means 50. However, it is possible to envisage a case where it is given by the means 50, should it be desired to servo-link the calculated tension to a previously calculated value of tension. This is the case notably when the servolink is not implemented from the very start of the reaction; the calculation of the interface tension starting with the formation of the drop, and the progress of the tension is followed at each instant of the calculation. Then, a value calculated at a given time is stored as a set-point value, and the servocontrol system is put into operation so as to tend to keep the interface tension in the vicinity of this calculated value;

FIG. 5 shows an exemplary practical embodiment of an apparatus according to the invention.

The drop-forming mechanism comprises a transparent (polycarbonate) measuring bowl 22 placed in a thermostatic chamber 24 made of aluminium alloy. A perforation at the bottom of the bowl enables a drop-forming needle to pass into the chamber. The needle is connected to an injection syringe 26, the piston 27 of which can be displaced automatically by a stepping motor 28, for example by means of a screw-nut system.

A light source 32, mounted on an optical stand 34 and placed on one side of the bowl 22, illuminates the drop 10. A video camera 36 with CCD sensor is placed on the other side of the chamber to enable the acquisition of an image of the drop. Naturally, the thermostatic chamber is cut out along on the path of the optical rays so that the drop can be observed through the walls of the bowl 22 which is transparent.

Preferably, the light source has a source proper, namely a laser or other source, and collimation lenses to form a parallel beam illuminating the drop. An objective is placed between the drop and the camera to define a desired magnification of the image of the drop.

The camera is the main element of the image acquisition means 30.

The video signal coming from the camera will be treated to extract the contour of the drop, then the interface tension will be calculated from the shape and dimensions of the drop and, finally, this tension will be regulated with respect to a set-point value. All these operations will be carried out by a computer programmed accordingly, this computer having an output capable of acting on the stepping motor 28.

A personal microcomputer will generally be enough to carry out these signal processing operations and calculations, but cases may be envisaged where the kinetics of the reaction are fast enough to require more substantial means of calculation. Indeed, it must be recalled that the principle of the invention requires real-time regulation to servolink the growth of the drop to a value of interface tension that is calculated in real time.

The video signal is digitized and stored in an image processing interface 42 coupled to a microcomputer 44. This interface has, in particular, a memory of the digitized image. In one example, a IMAGING TECHNOLOGY PFG 100+ image digitization electronic card may be used to digitize the signals delivered by a CCD camera from the firm RTC, reference 56470, fitted out with a BOYER 135 objective. A permanent display of the contents of the image memory may be made on a monitor 46 connected to the interface 42.

The microcomputer 44 is coupled to a control keyboard 48 and to a display screen 52. Finally, it has an output to control a power circuit 54 connected to the stepping motor 28.

The microcomputer permanently carries out the extraction of the coordinates of the points of the contour of the drop. From this, it gives a value of interface tension. This value is compared with a set-point value. If the value calculated is lower than the set-point value, the stepping motor is activated to inject an additional quantity of liquid.

With the computation means provided by personal microcomputers, and using sufficiently fast algorithms for the calculation of interface tension, it is possible for example to obtain an interface tension value approximately every second. For many studies of reactions in the presence of surface-active agents, this duration is short enough to enable real-time regulation of the quantity of liquid injected by the syringe.

One of the major pieces of data that can be gathered with this method according to the invention is the quantity of surface-active agents that migrate to the interface per unit of time. This quantity is indirectly measured from the increase in the surface area of drop needed per unit of time to keep the value of interface tension constant. The surface may be computed at each instant from the shape of the digitized contour stored in the memory.

A detailed description shall now be given of the preferred method according to the invention for obtaining a value of interface tension, a method that can be used quite advantageously whenever it is desired to obtain a value of tension speedily.

The method is applicable with a pendant drop or also a standing drop. It shall be described here below with reference to a pendant drop. Very slight adaptations are needed for a standing drop since the Laplace equation is slightly different.

The mathematical bases that justify the method are given here below with reference to FIG. 6 which recalls the notations used.

The coordinates of a point of the contour are defined with respect to the apex of the drop, namely the tip for a drop that is pointed upwards and the base for a drop that is hanging downwards. The parameter x is the horizontal abscissa of a point of the contour; the parameter z is the vertical ordinate of this point. The angle E is the angle formed with the horizontal by the tangent to the contour at the point having coordinates x, z.

The following is the Laplace formula which completely defines the contour of the drop:

$$(1/x).d(x \sin E)/dx = 2b - c.z$$

b is the radius of curvature at the apex; and
c is the constant of capillarity of the pair constituted by the liquid and the ambient medium;
$c = g.(D1-D2)/\text{gamma}$
where:
  g is the constant of gravity;
  D1-D2 is the difference in density between the liquid and the ambient medium; gamma is the interface tension sought If the Laplace equation is integrated from 0 to x, the following equation is arrived at:

$$x \sin E = x^2/b - c.\text{int}(x.z.dx)$$

where the expression int(x.z.dx) represents the integral from 0 to x of the product x.z.dx.

Now, this complex integral, which brings into play both the abscissa and the ordinate, is related in a certain way to the volume of the drop located between the apex and the ordinate z plane.

Indeed, this volume V(z) of the drop can be written in the form of the difference between the volume $V1(x,z) = \text{pi}.x^2.z$ of a main cylinder with a radius x and a height z and the sum V2(x,z) of the elementary volumes of hollow cylinders with a radius x, a thickness dx and a height z located between this main cylinder and the contour of the drop. This sum is precisely equal to 2pi.int(x.z.dx).

$$V(z) = pi.x^2.z - 2.pi.\text{int}(x.z.dx)$$

This enables the Laplace equation integrated from 0 to x to be written in the following form:

$$V(z) = pi.x^2.z - (2/c)(x^2/b - x. \sin E)$$

If the following equations are submitted:
  A=c/2 (inversely proportional to the interface tension gamma),
  B=1/b (inverse of the radius of curvature at the apex),
  $u = V(z)/pi - x^2.z$
  $v = x^2$
  $w = x.\sin E$
Then the Laplace equation integrated from 0 to x is expressed simply in the form:

$$A.u + B.v = w$$

This equation should naturally be verified whatever may be the value of the point having coordinates x and z, A and B being constants for a given shape of drop.

It will easily be understood that it is possible to find constants A and B by taking any two points on the contour of the drop and by calculating, for these two points, the triplets u', v', w' (first point) and u", v", w" (second point) and then by resolving the two equations with two unknown quantities A and B.

However, with two points, the precision is limited, as already explained with reference to the prior art, if only because of the digitization of the contour with limited precision.

The underlying idea of the invention is that of using all the points of the contour of the drop and of searching for the value of A and B that is best suited to all the equations A.u+B.v=w resulting therefrom.

It should then be possible to obtain high precision without its being necessary, for all that, to carry out repeated calculations of a theoretical shape of a drop as was done in the prior art. The calculation of the shape of a drop is indeed a lengthy calculation.

This is why the invention essentially proposes the following method for the measurement of interface tension:

- the shape of the drop is determined optically by the extracting of the coordinates x and z of the points of the contour of the drop (the number of points depends on the resolution of the optical sensor);
- for each point with an index i and with coordinates $x_i$, $z_i$, three values $u_i$, $v_i$, $w_i$ are calculated, bringing into play, apart from the known constants, solely the coordinates of the point i, the volume of the drop between the apex and the horizontal plane of ordinates $z_i$ and the angle with respect to the horizontal of the tangent to the drop at the point i;
- and the values of A and B that most efficiently verify the equation $A.u_i+B.v_i=w_i$ for all the points of the contour are determined.
- on the basis of A and of known constants, the interface tension gamma is computed.

It is consequently be noted that:

1./ it is not necessary to determine a theoretical shape of a drop on the basis of the integration of the Laplace equation; and it is even less necessary to do so several times in succession by iteration;

2./ the only integral to be colculated is the one related to the volume of the drop; and when going from one point to the next one, the integral uses the previously calculated volume so that there is not an integral to be made at each point but a simple addition if the calculation is made for points one after the other along the contour.

Furthermore, according to a particularly advantageous approach to the invention, it is possible to calculate the values A and B which most suitably verify the equations $A.u_i+B.v_i=w_i$ for all the points of the contour by means of a very simple method.

The method shall be given, followed by its mathematical justification.

At least five of the following squares and products are summed for all the points i: $u_i^2$, $v_i^2$, $u_iv_i$, $v_iw_i$, $w_iu_i$, $w_i^2$, the summations giving respectively the sum S1 of the squares $u_i^2$, the sum S2 of the squares $v_i^2$, the sums S3, S4, S5 of products $v_iv_i$, $v_iw_i$, $w_iu_i$ and the sum S6 of the squares $w_i^2$.

This is followed by the resolving of a system of two equations with two unknown quantities A and B taken from among the following three equations:

$$A.S1+B.S3=S5$$

$$A.S3+B.S2=S4$$

$$A.S5+B.S4=S6$$

and the interface tension gamma is calculated from the equation gamma=g.(D1-D2)/2.A.

The mathematical justification is based on the principle of the optimization of the choice of A and B by the least error squares method applied to the quantity $A.u_i+B.v_i-w_i$.

This method consists in saying that if the equality $A.u_i+B.v_i=w_i$ needs to be verified to the best possible extent for all the points, one solution is to minimize the sum of the squares of the errors on this equation, i.e. the sum of the squares of $(A.u_i+B.v_i-w_i)$.

First of all, if the equation $A.u_i+B.v_i=w_i$ were to be verified for all the values of i, the following equations would also be verified:

$$A.u_i^2+B.v_i.u_i=w_i.u_i \text{(multiplication by } u_i\text{)}$$

$$A.u_i+B.v_i^2=w_i.v_i \text{(multiplication by } v_i\text{)}$$

$$A.u_iw_i+B.v_i.w_i=w_i^2 \text{(multiplication by } w_i\text{)}$$

it being possible to rewrite these equations (multiplication by A and B respectively for the first two), as follows:

$$A^2.u_i^2+A.B.v_i.u_i=A.w_i.u_i$$

$$A.B.u_i.v_i+B^2.v_i^2=B.w_i.v_i$$

$$w_i^2=A.u_i.w_i+B.v_i.w_i$$

A verification will then also be carried out on the sum of these three equations, i.e.

$$A^2.u_i^2+2.A.B.v_i.u_i+B^2.v_i^2+w_i^2=2.A.u_i.w_i+2.B.w_i.v_i$$

which is nothing other than $$(A.u_i+B.v_i-w_i)^2=0$$

These means that the following three equations:

$$A.\ u_i^2+B.v_i.u_i=w_i.u_i$$

$$A.\ u_i.v_i+B.\ v_i^2=w_i.v_i$$

$$A.\ u_i.w_i+B.\ v_i.w_i=w_i^2$$

could then be replaced by any two of the three equations and the supplementary equation $$(A.u_i+B.v_i-w_i)^2=0$$

All these equations remain obviously true if they are summed up for all the points i.

The three equations then become:

$$A.S1+B.S3=S5$$

$$A.S3+B.S2=S4$$

$$A.S5+B.S4=S6$$

As for the additional equation, if it is summed for all the points i, it expresses precisely the condition of minimization of the sum of the error squares of the basic equation $A.u_i+B.v_i=w_i$ for all the points i.

In other words, this means that if the criteria of optimization of the choice of A and B is the least error squares method applied to the basic equation $A.u_i+B.v_i=w_i$, then A and B can be obtained quite simply by the resolving of two linear equations with two unknown quantities, chosen from among the following three:

$$A.S1+B.S3=S5$$

$$A.S3+B.S2=S4$$

$$A.S5+B.S4=S6$$

The solving of two equations with two unknown quantities is obviously simpler and faster than any other method of optimization by iteration.

This is what makes it possible to obtain a very fast measurement of the interface tension and, among other results, a possibility of real-time regulation as explained here above while, at the same time, bringing into play all the points of the contour of the drop.

With A being obtained, all that remains to be done is to calculate the interface tension gamma according to the relationship given further above between A and gamma. This value gamma is the value that can be taken as a measured magnitude introduced into the control unit 60. The set-point value may be a value of gamma measured at a certain instant after the start of the experiment.

Owing to the development of gamma, there is also the initial value of gamma available. Furthermore, when the servo-control system works, the quantity of surface-active agent absorbed per time unit is known, for example by counting the number of steps imposed on the motor during this time unit. However, preferably, the quantity of agent adsorbed is measured from the images themselves. Indeed, with all the elements being available, it is possible to calculate the surface of the drop from the image by assuming that the drop accepts the symmetry of a figure of revolution. Thus, there is a saving of a supplementary sensor.

We claim:

1. Method for the analysis of the behavior of an interface between a liquid and an immiscible fluid ambient medium comprising the controlled introduction of liquid into the ambient medium, a calculation and control of the interface tension between this liquid and this ambient medium, characterized in that it comprises an action of servocontrol on a mechanism for the introduction of the liquid in a direction tending to bring the interface tension to a desired value, and a measurement of characteristics of the physical reaction between this liquid and this ambient medium resulting from the liquid introduction from a measurement of the flow rate of introduction.

2. Method of analysis according to claim 1, characterized in that a drop of liquid is formed at the end of a needle inserted into the ambient medium, the shape and the dimensions of the drop are determined, the interface tension is calculated from this shape, the computed tension is compared with a desired value and action is taken on an injection mechanism coupled to the needle to inject an additional quantity of liquid into the drop if the interface tension is lower than the desired value.

3. Method according to claim 2, characterized in that when a drop is formed, the value of the interface tension of the drop is calculated at determined successive instants, without action on the injection of the liquid and, at a given instant, the interface tension calculated at this time is established as a desired value of interface tension, and the action of the injection mechanism is authorized and initiated by a user in order to subsequently keep the value of interface tension, calculated during the reaction, at this desired value.

4. Method according to one of the claims 2, characterized in that the flow rate is measured from the shape and the dimensions of the drop.

5. Method according to one of the claims 1, characterized in that the liquid and/or the ambient medium contain a surface-active agent.

6. Apparatus for the analysis of the interface behavior of a liquid in a fluid ambient medium, comprising a means to form a drop of liquid in an ambient medium contained within chamber walls, a means to analyze the shape and dimensions of the drop, a means to calculate the interface tension from the shape and dimensions of the drop, characterized in that it further comprises a means to modify the quantity of liquid injected into the drop as a function of the divergence between the calculated interface tension and a desired value of interface tension and a means to measure the injected quantity.

7. Apparatus according to claim 6, characterized in that the means to modify the quantity of liquid comprises a syringe connected to a needle penetrating the ambient medium, and a stepping motor to activate the syringe.

8. Apparatus according to claim 6 including a means to compare the calculated interface tension with a fixed set-point value, the fixed set-point value being a previously-calculated interface tension value.

9. Apparatus according to claim 6, characterized in that the means for measuring the quantity injected also includes means capable of measuring the shape and dimensions of the drop.

10. Apparatus according to claim 6, including means to enable initially a calculation of the interface tension without a physical reaction resulting from the quantity of liquid injected, means to store the calculated tension with a view to using it subsequently as a set-point value, and means to then calculate the interface tension intermittently in a periodic manner and modify the quantity of liquid injected after each period in a direction tending to reduce the divergence between the calculated tension and the set-point value.

11. Method to measure the interface tension gamma between a drop of liquid and an ambient medium, for the application of the method according to claim 1, comprising the following operations:

the shape of the drop is determined optically by the extracting of the coordinates x and z of the points of the contour of the drop for each point with an index i and with coordinates $x_i$, $z_i$, three values $u_i$, $v_i$, $w_i$ are calculated, bringing into play, apart from the known constants, solely the coordinates of the point i, the volume of the drop between the apex and the horizontal plane of ordinates $z_i$ and the angle with respect to the horizontal of the tangent to the drop at the point i;

and the values of A and B that most efficiently verify the equation $A.u_i+B.v_i=w_i$ for all the points of the contour are determined;

the interface tension gamma which is inversely proportional to A is calculated on the basis of A, the difference in density between the liquid and the ambient medium, and the constant of gravity.

12. Method according to claim 11, characterized in that at least five of the following squares and products are summed for all the points i: $u_i^2$, $v_i^2$, $u_iv_i$, $v_iw_i$, $w_iu_i$, $w_i^2$, the summations giving respectively the sums S1, S2, S3, S4, S5, S6, then there is resolved a system of two equations with two unknown quantities A and B taken from among the following three equations:

$$A.S1 + B.S3 = S5$$

$$A.S3 + B.S2 = S4$$

$$A.S5 + B.S4 = S6$$

where the method permits a choice of any two equations from the three listed above and the interface tension gamma is calculated from the equation gamma=g.(D1-D2)/2.A, where g is the constant of gravity and D1-D2 is the difference in density between the liquid and the ambient medium.

13. Method according to one of the claims 11, characterized in that:

$x_i$ and $z_i$ are the horizontal coordinates of a point i of the contour with respect to the apex of the drop;

$u_i$ is the difference between, on the one hand, the partial volume of the drop divided by the number Pi and, on the other hand, the product $x_i^2 . z_i$;

$v_i$ is the square $x_i^2$ $w_i$ is the product of $x_i$ by the sine of the angle E formed with the horizontal by the tangent to the contour at the point indexed i.

14. Method according to claim 2, characterized in that a measurement is made of a magnitude representing the variation of the volume of liquid injected into the drop per unit of time, by comparing the images of this drop at successive instants.

15. Method according to claim 2, characterized in that a measurement is made of a magnitude representing the variation of the surface of the drop by comparing the images of this drop at successive instants.

* * * * *